(12) United States Patent
Nicozisis

(10) Patent No.: US 7,011,517 B2
(45) Date of Patent: Mar. 14, 2006

(54) APPARATUS AND METHOD FOR REMOVING A REMOVABLE TOOTH POSITIONING APPLIANCE FROM THE TEETH OF A PATIENT

(75) Inventor: Jonathan L. Nicozisis, Lancaster, PA (US)

(73) Assignee: Nickpick Enterprises, LLC, Princeton, NJ (US)

( * ) Notice: Subject to any disclaimer, the term of this patent is extended or adjusted under 35 U.S.C. 154(b) by 178 days.

(21) Appl. No.: 10/666,163

(22) Filed: Sep. 19, 2003

(65) Prior Publication Data

US 2005/0064358 A1    Mar. 24, 2005

(51) Int. Cl.
    *A61C 3/00*        (2006.01)
(52) U.S. Cl. .......................................... 433/3; 433/141
(58) Field of Classification Search ..................... 433/2, 433/3, 141, 148, 150
    See application file for complete search history.

(56) References Cited

U.S. PATENT DOCUMENTS

| | | | |
|---|---|---|---|
| 1,389,954 A * | 9/1921 | McCombs ................. | 433/141 |
| 2,602,998 A * | 7/1952 | Sprague ..................... | 433/141 |
| 3,060,582 A * | 10/1962 | Kopp ......................... | 433/141 |
| 3,360,861 A * | 1/1968 | Hoffman ..................... | 433/3 |
| 4,609,353 A | 9/1986 | Kline | |
| 4,627,817 A | 12/1986 | Higa | |
| 4,904,183 A * | 2/1990 | Hannan et al. ................. | 433/3 |
| 4,975,051 A * | 12/1990 | Kargas et al. ................. | 433/3 |
| 5,039,302 A * | 8/1991 | Keys ............................ | 433/3 |
| 5,197,878 A | 3/1993 | Lukase | |
| 5,487,660 A | 1/1996 | Good | |
| 5,839,896 A | 11/1998 | Hickok | |
| 6,183,248 B1 | 2/2001 | Chishti | |
| 6,280,184 B1 | 8/2001 | Hamilton | |
| 6,390,812 B1 | 5/2002 | Chishti | |
| 6,413,086 B1 | 7/2002 | Womack | |
| 6,458,298 B1 | 11/2002 | Chishti | |
| 2002/0051951 A1 | 5/2002 | Chishti | |
| 2002/0142258 A1 | 10/2002 | Chishti | |
| 2003/0186184 A1 | 10/2003 | Chishti | |

* cited by examiner

*Primary Examiner*—Ralph A. Lewis
(74) *Attorney, Agent, or Firm*—Brian L. Belles; Wolf, Block, Schorr & Solis-Cohen, LLP

(57) ABSTRACT

An apparatus, system, and method of removing removable tooth positioning appliances, such as aligners, from the teeth of a patient. In one aspect, the invention is an apparatus for removing a removable tooth positioning appliance from teeth of a patient comprising: a handle portion; a member extending from the handle portion and having a distal end; and an engagement block having a tapered edge for engaging an edge of the tooth positioning appliance, the engagement block protruding from the member at or near the distal end.

15 Claims, 5 Drawing Sheets

APPARATUS AND METHOD FOR REMOVING A REMOVABLE TOOTH POSITIONING APPLIANCE FROM THE TEETH OF A PATIENT

TECHNICAL FIELD OF THE INVENTION

The present invention relates generally to the field of orthodontics, and specifically to improved orthodontic tools for removing removable tooth positioning appliances.

BACKGROUND OF THE INVENTION

As an alternative to braces and other bonded orthodontic equipment, removable tooth positioning appliances, such as aligners and retainers, that tightly fit over teeth are commonly employed in orthodontic treatments for controlled tooth movement to a pre-determined position. These tooth positioning appliances are removable in that they are not bonded to the teeth which they are used to manipulate. In providing such appliances and treatments, it is important to move teeth to an ideal pre-determined position with gentle controlled forces. Typically, the appliance is fabricated to provide accuracy of placement in compliance with the exact shape of the teeth or the exact shape and placement of attachment devices. An example of such a removable tooth positioning appliance can be found in U.S. Pat. No. 6,183,248, Chishti, et al., which is incorporated herein in its entirety by reference.

Removable tooth positioning appliances comprise a thin shell of material that generally conforms to a patient's teeth but is slightly out of alignment with the initial tooth configuration. By properly choosing the configuration, placement of the appliance over the teeth will move individual teeth to desired intermediate or final positions over time. Depending on the number of teeth that are malaligned, these positioning appliances can be designed to fit over any number of teeth, and often are designed to be placed over the entire top or bottom set of teeth.

The repositioning forces required to move a tooth from one position to another position in a reasonable amount of time may be formidable. To achieve such forces, these tooth positioning appliance must be relatively stiff (i.e. possess a high strength or high modulus) to provide a sufficient grip on the teeth. The stiffness both ensures that the dental appliance remains firmly in position on the patient's teeth and provides the repositioning force necessary to move the teeth. The stiffness also permits the positioning appliance to grab hold of an anchor device or other surface feature which may be present on the tooth to apply a directed force to execute orthodontic tooth movements.

While stiffness of the tooth positioning appliance is desirable for providing repositioning forces and for maintaining appliance position on the teeth, the removal of such appliances can be difficult. The requirement that the appliance tightly conform to the teeth of the patient makes it even more difficult to remove these appliances. However, periodic removal of the positioning appliance is desirable for a number of purposes including cleaning, dental hygiene, removal before meals, removal for cosmetic purposes, and removal and replacement in the course of treatment. Unassisted removal by patients themselves is often very difficult. In most or all of these cases, however, it will be inconvenient for the patient to visit the practitioner. As a result, patients will use household instruments, such as forks, etc., to remove the tooth positioning appliance. The use of such make-shift instruments can damage both the patient's teeth or gums and the appliance itself. Moreover, even if the patient can visit a practitioner to remove the tooth positioning appliance, practitioners use orthodontic instruments designed for other uses to remove the appliance. These orthodontic appliances often present the same problems as the patient's make-shift instruments.

For these reasons, it would be desirable to provide a tool that is specifically designed to remove such tooth positioning appliances from a patient's teeth in a safe, effective, and efficient manner.

DISCLOSURE OF THE INVENTION

It is therefore and object of the present invention to provide an apparatus, system, and method for improved removal of removable tooth positioning appliances from the teeth of a patient.

A further object is to provide an apparatus, system, and method for removing a removable tooth positioning appliances from the teeth of a patient that reduces damage to the patient's teeth or gums.

Yet another object is to provide an apparatus, system, and method for removing a removable tooth positioning appliances from the teeth of a patient that reduces damage or wear to tooth positioning appliance.

Still another object is to provide an apparatus, system, and method for removing a removable tooth positioning appliances from the teeth of a patient that is inexpensive and/or easy to manufacture.

A still further object is to provide an apparatus, system, and method for removing a removable tooth positioning appliances from the teeth of a patient that reduces the amount of time and/or effort it takes to complete such removal.

These objects and others are met by the present invention which in one aspect is an orthodontic apparatus that is specifically designed to be capable of engaging an edge of a removable tooth positioning appliance so that force can be applied to the appliance for its removal from the teeth. The invention, in this aspect, is an apparatus comprising: a handle portion; a member extending from the handle portion and having a distal end; and an engagement block having a tapered edge for engaging an edge of the tooth positioning appliance, the engagement block protruding from the member at or near the distal end.

Preferably, the apparatus further comprises a stop block protruding from the member so as to form a recess with the engagement block. In using this embodiment of the apparatus to remove the appliance, the edge of the appliance will slide into the recess.

The engagement block and the stop block preferably protrude from the member at an approximately 90 degree angle. Additionally, the member will preferably have a substantially L-shaped section having a vertical portion and a horizontal portion. In this embodiment, the distal end will be located on the horizontal portion. This configuration makes it easier for the tapered edge of the engagement block to be properly positioned near the edge of the tooth positioning appliance which is at or near the gum line. The apparatus can be constructed of plastic, metal, wood, epoxy, nylon, or any other suitably rigid material.

It is further preferably for the member to have a substantially rectangular cross-section and that the distal end of the member comprises a planar surface. A planar surface on the distal end is preferred because this surface contacts the teeth and gums of the patient during removal of the appliance. By having the surface planar, the danger of damaging the gums or teeth is minimized. Finally, the tapered edge of the engagement bar can take on a variety of profiles. For example, the tapered edge can be tapered away from the distal end, tapered toward the distal end, or a combination of the two.

In another aspect, the invention is a dental system for positioning teeth comprising: a removable tooth positioning appliance for aligning teeth of a patient; and an apparatus comprising a handle portion, a member extending form the handle portion and having a distal end, and an engagement block having a tapered edge for engaging an edge of the tooth positioning appliance, the engagement block protruding from the working portion at or near the distal end. Preferably, the removable tooth positioning appliance is an aligner that fits over a plurality of teeth. The system can be designed so that the apparatus has any or all of the characteristics described above.

In yet another aspect, the invention is a method of removing a removable tooth positioning appliance from teeth of a patient comprising: providing an apparatus having a handle portion, a member extending from the handle portion and having a distal end, and an engagement block having a tapered edge, the engagement block protruding from the member at or near the distal end; positioning the tapered edge of the member near an edge of the tooth positioning appliance; inserting the tapered edge between the tooth positioning appliance and the teeth of the patient; and exerting force to the handle portion thereby causing the tooth positioning to release from the teeth of the patient. Preferably, the force exerted to the handle portion is in a direction substantially parallel to the teeth of the patient. This helps keep the teeth and gums from being damaged.

MODES FOR CARRYING OUT THE INVENTION

Figure 1:
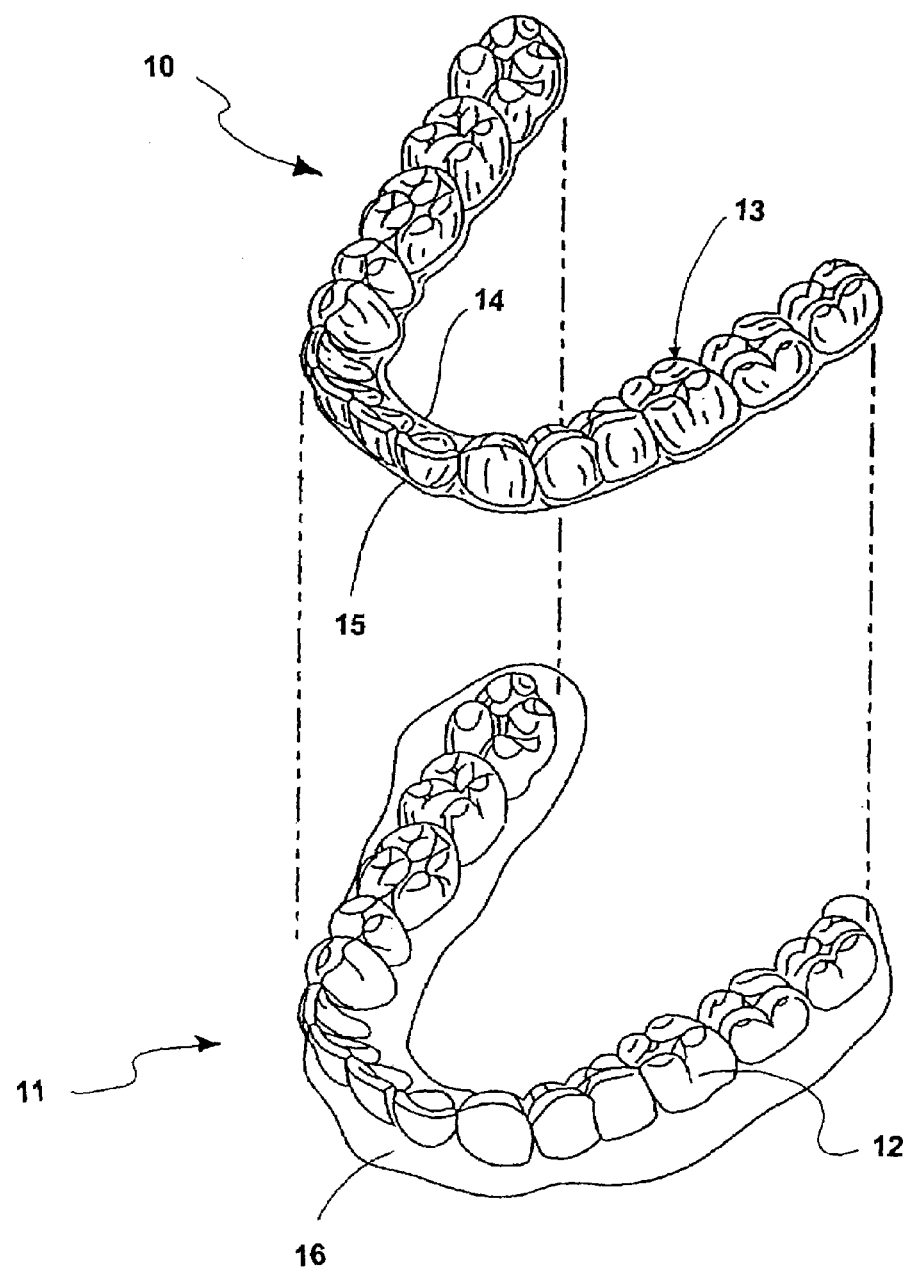
FIG. 1 is a top perspective view of an embodiment of a tooth positioning aligner used with in an embodiment of the system of the present invention.

Referring first to FIG. 1, aligner 10 is illustrated aligned with a lower jaw 11 for application. Aligner 10 is removably replaceable over the teeth 12. The aligner 10 is intended to effect incremental repositioning of individual teeth 12 in the lower jaw 11. A full description of an exemplary repositioning appliance is described in U.S. Pat. No. 5,975,893, Chishti et al., which is herein incorporated by reference for all purposes.

Aligner 10 includes a polymeric shell 13 forming an inner cavity, a proximal edge 14, and a distal edge 15. The cavity formed by shell 13 is shaped to receive and resiliently reposition 9 set of teeth 12 from one tooth arrangement to a successive tooth arrangement. Aligner 10 will preferably, but not necessarily, fit over all teeth 12 present in the upper or lower jaw 11 (only the lower jaw is illustrated). Often, only certain one(s) of the teeth 12 will be repositioned while others of the teeth 12 will provide a base or anchor region for holding the aligner 10 in place as it applies the resilient repositioning force against the tooth or teeth 12 to be repositioned. The gums 16 and/or the palette can also serve as an anchor region, thus allowing all or nearly all of the teeth 12 to be repositioned simultaneously. Additionally, anchors and adhesives, are available which may also serve as attachment points for aligner 10.

Aligner 10 is forced down over teeth 12, typically by the patient biting down on the shell 13 or by other forms of manual pressure being applied to the shell 13. Edges 14 and 15 are made to engage what is known as the undercut of the teeth 12. Typically, this type of engagement is helpful in that it allows for specific tooth movements, such as extrusions (i.e. occlusal movement of the tooth). However, this tight fit presents problems in that it is difficult to remove aligner 10 from the teeth 12 once it is in place.

Figure 2:
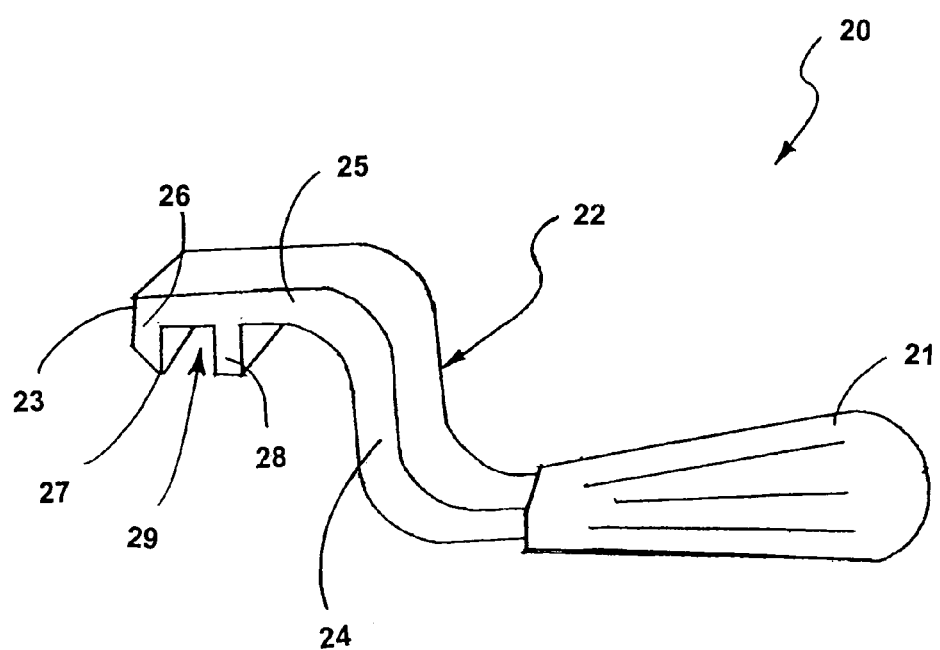
FIG. 2 is a top perspective view of an embodiment of an orthodontic tool according to the present invention.
Figure 3:
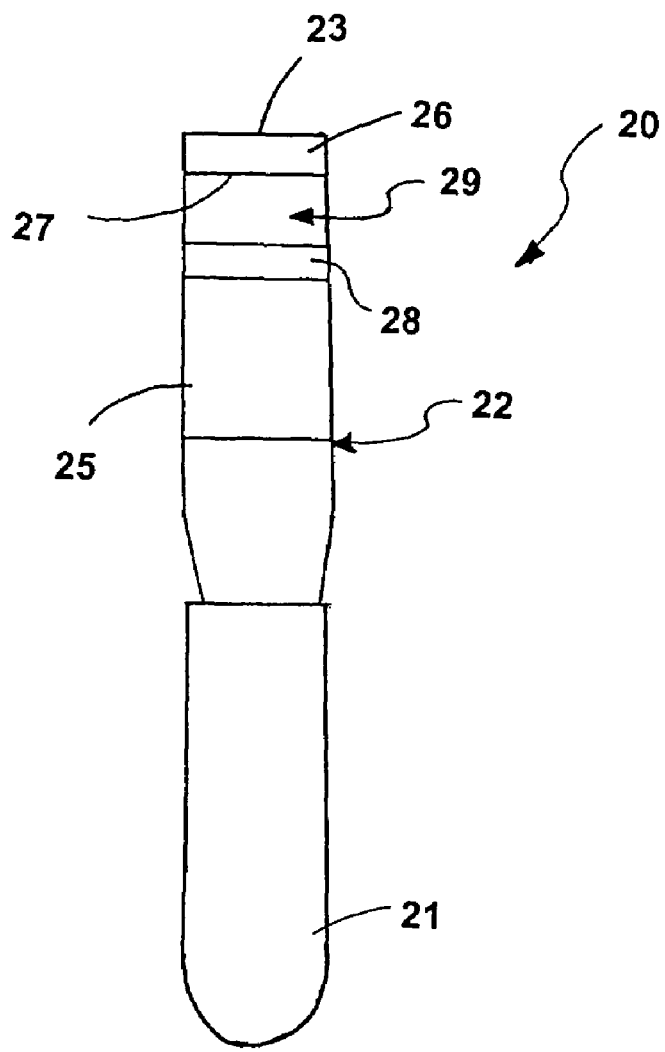
FIG. 3 is a bottom view of the orthodontic tool of FIG. 2.

Referring now to FIGS. 2 and 3, orthodontic tool 20, according to an embodiment of the present invention, is illustrated. Orthodontic tool 20 is designed to easily remove aligner 10 from the teeth of a patient by engaging distal edge 15 of aligner 10 and separating aligner 10 from teeth 12 (illustrated in FIG. 5). Orthodontic tool 20 has a handle 21 and a member 22 extending from the handle 21. Member 22 can be either integral with handle 21 or can be a separate piece coupled to the handle. Member 22 has distal end 23 at the end opposite the portion of member 22 that extends from handle 21. Distal end 23 is a planar surface. Member 22 has a substantially L-shaped portion consisting of vertical portion 24 and horizontal portion 25. Distal end 23 is at the end of horizontal portion 25.

Figure 5:
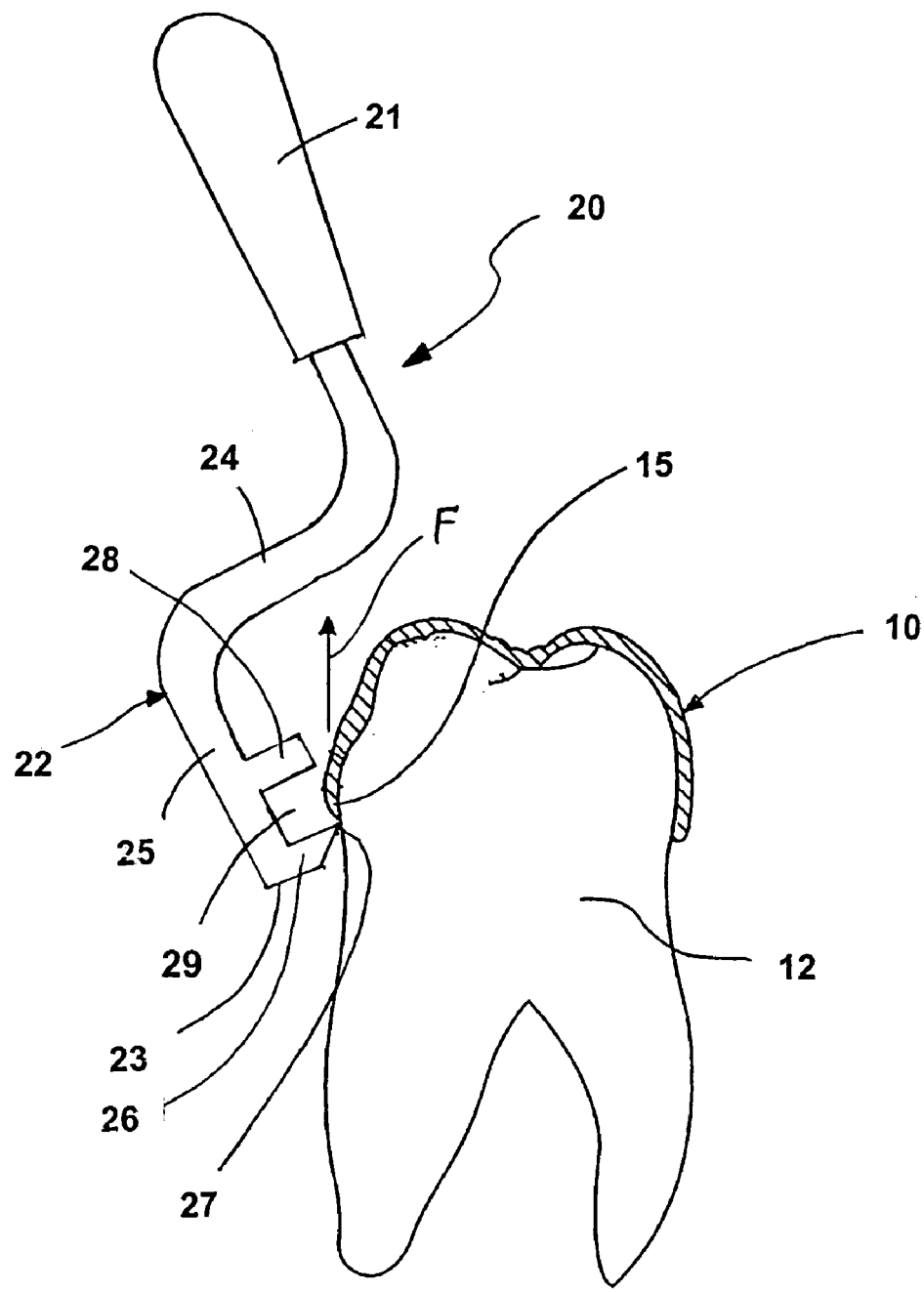
FIG. 5 is a side view of an embodiment of the orthodontic tool of FIG. 2 being used to remove the tooth positioning aligner of FIG. 1 from a tooth, the aligner and tooth being shown in cross-section

Engagement block 26 is located at or near distal end 23. Engagement block 26 protrudes downwardly from horizontal portion 25 of member 22 at an approximately 90 degree angle. Engagement block 26 terminates in a tapered edge 27. By tapering engagement block 26 to a tapered edge 27, engagement of distal edge 15 of aligner 10 is facilitated for removal (FIG. 5). Orthodontic tool 20 further includes stop block 28 protruding from horizontal portion 25 of member 22. Stop block 28 protrudes from member 22 so as to form recess 29 with engagement block 26. During the engagement and removal process of aligner 10, distal edge 15 of aligner 10 will fit into recess 29.

Figure 4A:
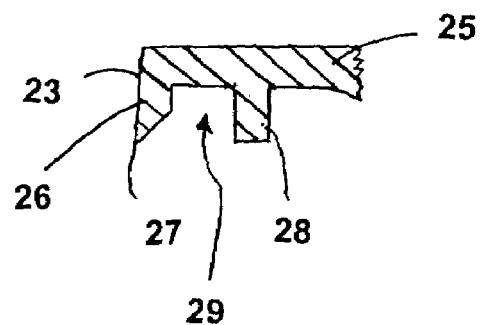
FIG. 4A is a side cross-sectional view of a first alternative embodiment of a tapered edge for an orthodontic tool according to the present invention.
Figure 4B:
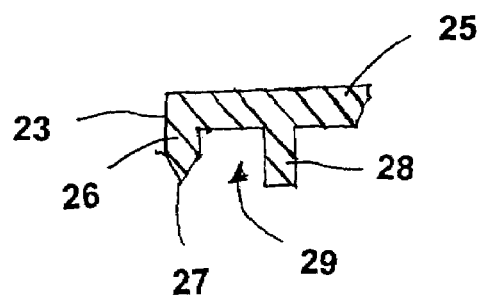
FIG. 4B is a side cross-sectional view of a second alternative embodiment of a tapered edge for an orthodontic tool according to the present invention.

In the illustrated embodiment, engagement block 27 is tapered away from distal edge 23 to form tapered edge 27. However, alternative tapering profiles are possible. For example, referring to FIGS. 4A and 4B, two different tapered profiles are illustrated. In FIG. 4A, engagement block 26 is tapered toward the distal edge 23 so that tapered edge 27 is flush with the distal edge 23. In FIG. 4B, engagement block is tapered at its end both toward and away from distal end 23 so as to form tapered edge 27 at or near the center of engagement block 26.

Referring now to FIG. 5, orthodontic tool 20 is illustrated in a position to engage and remove aligner 10 from the teeth 12 of a patient. In using orthodontic tool 20 to remove aligner 10 from the teeth 12 of a patient, the orthodontic tool 20 is positioned so that tapered edge 27 of engagement block 26 is under distal edge 15 of aligner 10, which is close to the gum line. Once orthodontic tool 20 is manipulated so that tapered edge 27 engages distal edge 15 of aligner 10, upward force F is applied to the handle 21 by the patient. As this is done, tapered edge 27 is forced between the aligner 10 and teeth 12, causing distal edge 15 of aligner 10 into recess 29. Stop block 28 acts as a safety stop in case of slipping or other misapplied force. By continuing the application of force F, aligner 10 is dislodged and removed from the teeth 12 of the patient in a safe and effective manner.

The foregoing discussion discloses and describes merely exemplary embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A dental system for positioning teeth comprising:
    a removable tooth positioning appliance for aligning teeth of a patient; and
    an apparatus comprising a handle portion, a member extending form the handle portion and having a distal end, and an engagement block having a tapered edge for engaging an edge of the tooth positioning appliance, the engagement block protruding from the working portion at or near the distal end.

2. The system of claim 1 wherein the removable tooth positioning appliance is an aligner that fits over a plurality of teeth.

3. The system of claim 2 wherein the apparatus further comprises a stop block protruding from the member so as to form a recess with the engagement block, the recess adapted to receive the edge of the tooth positioning appliance when the tapered edge is used to remove the tooth positioning appliance from the teeth of the patient; the engagement block protruding from the member at an approximately 90 degree angle; the member comprising a substantially L-shaped section having a vertical portion and a horizontal portion, the distal end being located on the horizontal portion; the distal end of the member having a planar surface; and the wherein the tapered edge is tapered toward the distal end.

4. The system of claim 1 wherein the engagement block of the apparatus has a substantially rectangular cross section.

5. The system of claim 1 wherein the engagement block protrudes from the member at an approximately 90 degree angle.

6. The system of claim 1 wherein the apparatus is constructed of plastic.

7. The system of claim 1 wherein the tapered edge of the apparatus is tapered away from the distal end.

8. The system of claim 1 wherein the tapered edge of the apparatus is tapered toward the distal end.

9. A method of removing a removable tooth positioning appliance from teeth of a patient comprising:
    providing an apparatus having a handle portion, a member extending from the handle portion and having a distal end, and an engagement block having a tapered edge, the engagement block protruding from the member at or near the distal end;
    positioning the tapered edge of the member near an edge of the tooth positioning appliance;
    inserting the tapered edge between the tooth positioning appliance and the teeth of the patient; and
    exerting force to the handle portion thereby causing the tooth positioning to release from the teeth of the patient.

10. The method of claim 9 wherein the force exerted to the handle portion is in a direction substantially parallel to the teeth of the patient.

11. The method of claim 10 wherein the apparatus further comprises a stop block protruding from the member so as to form a recess with the engagement block, the recess adapted to receive the edge of the tooth positioning appliance when the tapered edge engages the tooth positioning appliance; the engagement block protruding from the member at an approximately 90 degree angle; the member comprising a substantially L-shaped section having a vertical portion and a horizontal portion, the distal end being located on the horizontal portion; the distal end of the member having a planar surface; and the wherein the tapered end is tapered toward the distal end.

12. The method of claim 9 wherein the engagement block protrudes from the member at an approximately 90 degree angle.

13. The method of claim 9 wherein the apparatus is constructed of plastic.

14. The method of claim 9 wherein the tapered edge of the apparatus is tapered away from the distal end.

15. The method of claim 9 wherein the tapered edge of the apparatus is tapered toward the distal end.

* * * * *

UNITED STATES PATENT AND TRADEMARK OFFICE
CERTIFICATE OF CORRECTION

PATENT NO. : 7,011,517 B2  Page 1 of 1
DATED : March 14, 2006
INVENTOR(S) : Jonathan L. Nicozisis It is certified that error appears in the above-identified patent and that said Letters Patent is hereby corrected as shown below:

Column 5,
Line 19, after "extending", delete "form".
Line 19, after "extending", insert -- from --.
Line 22, after "protruding from the", delete "working".
Line 23, before "at or near", delete "portion".
Line 23, before "at or near" insert -- member --.

Signed and Sealed this

Twenty-third Day of May, 2006

JON W. DUDAS
*Director of the United States Patent and Trademark Office*